US00PP32157P2

(12) United States Plant Patent
Lee

(10) Patent No.: US PP32,157 P2
(45) Date of Patent: Sep. 1, 2020

(54) ***PENTAS* PLANT NAMED 'PEZZ0012'**

(50) Latin Name: *Pentas lanceolata*
Varietal Denomination: PEZZ0012

(71) Applicant: SYNGENTA CROP PROTECTION AG, Basel (CH)

(72) Inventor: Jaemin Lee, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,598

(22) Filed: May 6, 2019

(51) Int. Cl.
*A01H 5/02* (2018.01)
*A01H 6/76* (2018.01)

(52) U.S. Cl.
USPC ..... Plt./466
CPC ..... *A01H 6/76* (2018.05)

(58) Field of Classification Search
USPC ..... Plt./466
CPC ..... A01H 6/76; A01H 5/02
See application file for complete search history.

*Primary Examiner* — Keith O. Robinson
(74) *Attorney, Agent, or Firm* — Dale Skalla

(57) ABSTRACT

A new *Pentas* plant named 'PEZZ0012' particularly distinguished by the large sized inflorescences and flowers, with deep rose flowers, dark-green foliage, upright, sturdy and vigorous growth habit, thick stems and branches on a well-branched plant, tolerates hot summer conditions with continuous summer flowering.

1 Drawing Sheet

Latin name of the genus and species of the plant claimed: *Pentas lanceolata.*

Varietal denomination: 'PEZZ0012'.

BACKGROUND OF THE NEW PLANT

The present invention comprises a new *Pentas*, botanically known as *Pentas lanceolata*, and hereinafter referred to by the variety name 'PEZZ0012'.

'PEZZ0012' is a product of a planned breeding program. The new cultivar 'PEZZ0012' has large sized inflorescences and flowers, with deep rose colored flowers, dark green foliage, upright, sturdy and vigorous growth habit, thick stems and branches on a well-branched plant, tolerates hot summer conditions with continuous summer flowering.

'PEZZ0012' originates from a cross hybridization of two sibling seedlings in a breeding program made in October 2012 in a greenhouse in Gilroy, Calif. The female parent was identified as 'PUA0550-1', not patented, with pink bicolor flowers.

The male parent was an unpatented plant identified as 'PUA0538-1' with light violet colored flowers. The resultant seed was sown in June 2013 in Gilroy, Calif.

'PEZZ0012' was selected as one flowering plant within the progeny of the stated cross in November 2013 in a greenhouse in Gilroy, Calif.

The first act of asexual reproduction of 'PEZZ0012' was accomplished when vegetative cuttings were propagated from the initial selection in November 2013 in a greenhouse in Gilroy, Calif.

BRIEF SUMMARY OF INVENTION

Horticultural examination of plants grown from cuttings of the plant initiated in November 2018 in Gilroy, Calif., and continuing thereafter, has demonstrated that the combination of characteristics as herein disclosed for 'PEZZ0012' are firmly fixed and are retained through successive generations of asexual reproduction.

'PEZZ0012' has not been observed under all possible environmental conditions. The phenotype may vary significantly with variations in environment such as temperature, light intensity, and day length.

A Plant Breeder's Right for this cultivar has not yet been applied for. 'PEZZ0012' has not been made publicly available prior to the effective filing date of this application, notwithstanding any disclosure that may have been made less than one year prior to the effective filing date of this application by the inventor or another who obtained 'PEZZ0012' directly from the inventor.

BRIEF DESCRIPTION OF THE PHOTOGRAPHS

Figure 1:
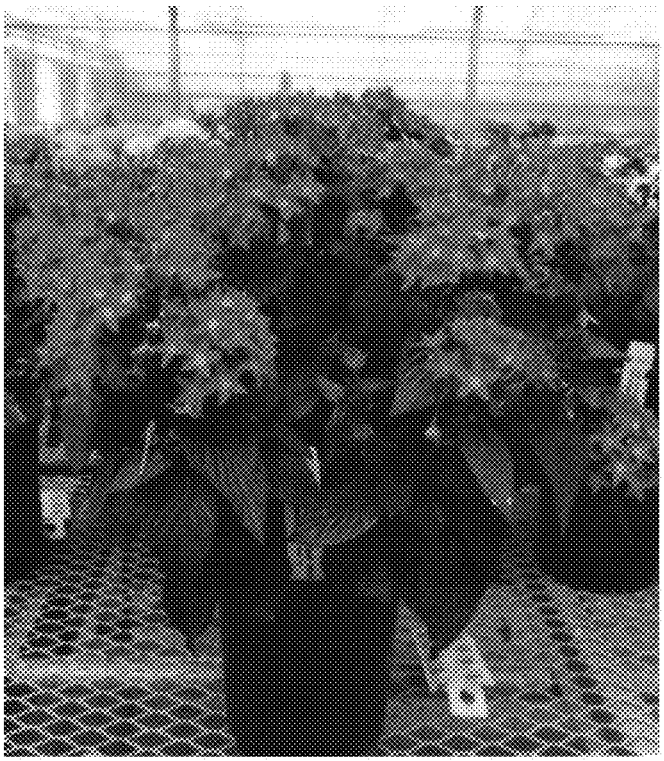
Figure 2:
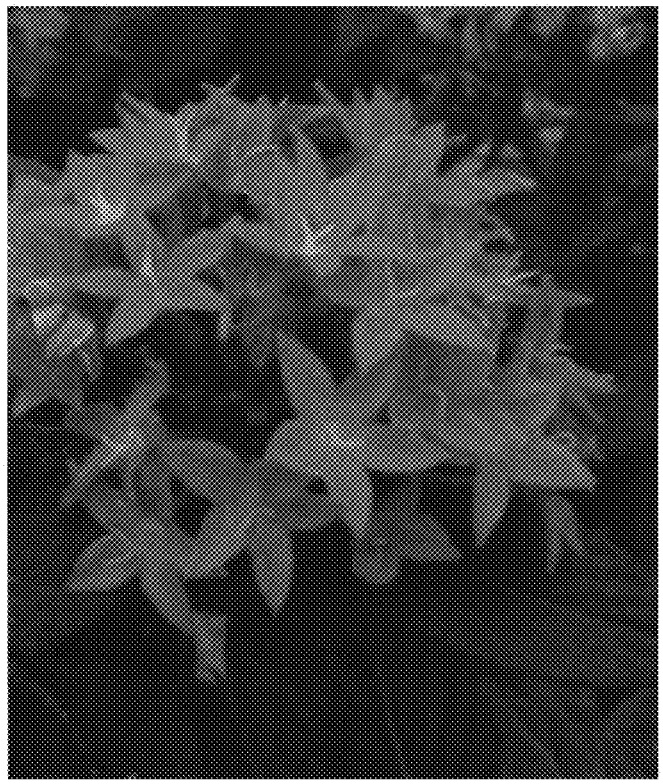

The accompanying photographic drawings show typical flower and foliage characteristics of 'PEZZ0012' with colors being as true as possible with an illustration of this type. The photographic drawings show in FIG. 1. a flowering plant of the new variety and in FIG. 2. a close-up of an inflorescence.

DETAILED BOTANICAL DESCRIPTION

The plant descriptions and measurements were taken in Gilroy, Calif. in early September under natural light. These plants were approximately 30 weeks old and were grown in a 1 gallon pot grown first in a greenhouse trial and then outside for about the last 10-12 weeks. The plants shown in the photographs were about 17 weeks old growing in a gallon pot in a greenhouse trial. The photographs were taken in April 2019.

Color references are made to The Royal Horticultural Society Colour Chart (R.H.S.) 2001.

TABLE 1

DIFFERENCES BETWEEN THE NEW VARIETY 'PEZZ0012' AND A MOST SIMILAR VARIETY

| | 'PEZZ0012' | 'Bismarck Pink' (U.S. Plant Pat. No. 15,780) |
|---|---|---|
| Flower color: | Deep rose | Pink |
| Plant height: | Taller | Shorter |
| Plant width: | About 34.0 cm | About 28 cm |

Plant:

*Form, growth and habit.*—Upright, sturdy and vigorous growth habit; good heat tolerance with continuous flowering through summer; thick stems and branches with a well-branched plant habit.

*Plant height.*—About 33.0 cm.

*Plant height (inflorescence included).*—About 36.0-38.0 cm.

*Plant width.*—About 34.0 cm.

Roots:

*Number of days to initiate roots.*—12-14 days at about 22 degrees C.

*Number of days to produce a rooted cutting.*—4-5 weeks at 22 degrees C.

*Type.*—Fine, fibrous, free branching.

*Color.*—RHS N155B.

Foliage:

*Immature leaf, color upper surface.*—Closest to RHS 139A.

*Immature leaf, lower surface.*—Closest to RHS 146A.

*Mature leaf, color upper surface.*—Closest to RHS 139A.

*Mature leaf, color lower surface.*—Closest to RHS 146A.

*Length.*—7.5-8.5 cm.

*Width.*—3.5-4.2 cm.

*Shape.*—Ovate.

*Base shape.*—Attenuate.

*Apex shape.*—Acute.

*Margin.*—Entire.

*Texture upper side.*—Hirsute.

*Texture lower side.*—Hirsute and more heavily on the veins.

*Color of veins, upper surface.*—RHS 146B.

*Color of veins, lower surface.*—RHS 147C.

*Pattern of veining.*—Pinnate.

*Petiole color.*—RHS 145A.

*Petiole length.*—1.2-1.5 cm.

*Diameter of petiole.*—0.2-0.3 cm.

*Texture.*—Hirsute.

Stem:

*Quantity of branches.*—7-8.

*Color of stem.*—RHS 152A.

*Length of stem.*—15-18.5 cm.

*Anthocyanin coloration of the stem.*—Present.

*Diameter.*—0.8-1.0 cm.

*Length of internodes.*—3-4.0 cm.

*Texture.*—Hirsute, pilose.

Peduncle:

*Color of peduncle.*—RHS 148B.

*Length of peduncle (cm).*—6-8 cm.

*Peduncle diameter (cm).*—0.2-0.3 cm.

*Peduncle texture.*—Pilose, hirsute.

Pedicel:

*Color of pedicel.*—RHS 138C.

*Length of pedicel.*—0.8-1 cm.

*Diameter of pedicel.*—0.2 cm.

*Pedicel texture.*—Pilose, hirsute.

Bud (just before opening):

*Color.*—RHS 64A.

*Length.*—1.5-1.7 cm.

*Width.*—0.3 cm.

*Shape.*—Elliptical.

Inflorescence:

*Type.*—Terminal corymb; but more umbel looking.

*Natural flowering.*—Late spring and summer, flowers continuously.

*Number of inflorescences per plant.*—18-20 with open flowers and 9-10 immature with only buds.

*Fragrance.*—None.

*Inflorescence diameter.*—9-10 cm.

*Inflorescence depth.*—4-4.5 cm.

Corolla:

*Form.*—Single, tubular-shaped flowers consisting of a single whorl of 5 pointed petals fused at the base; aspect slightly cupped; very free flowering.

*Lastingness of individual flowers.*—About 3-4 weeks depending on temperature.

*Immature.*—

*Color upper petals, upper surface.*—Closest to RHS 67A.

*Color upper petals, lower surface.*—Closest to RHS 64C.

*Mature.*—

*Diameter of floret.*—2.0-2.1 cm.

*Depth of floret.*—2.2-2.5 cm.

*Color upper petals, upper surface.*—Closest to RHS 64B.

*Color upper petals, lower surface.*—Closest to RHS 67C.

*Length petals.*—1.0-1.1 cm.

*Width of petals.*—0.5-0.55 cm.

*Petal shape.*—Ovate.

*Apex shape.*—Almost cuspidate.

*Margin.*—Entire.

*Base.*—Fused.

*Petal texture, upper surface.*—Papillose.

*Petal texture, lower surface.*—Papillose, with some hairs down the mid-vein.

*Corolla tube color, inside.*—Closest to RHS 69C.

*Corolla tube color, outside.*—Closest to RHS N74A.

*Corolla tube length.*—About 1.5 cm.

*Corolla tube diameter.*—0.3-0.4 cm.

*Corolla tube texture, inside.*—Very hirsute at throat with hairs running the length of the tube.

*Corolla tube texture, outside.*—Hiruste.

*Corolla throat diameter.*—0.4-0.5 cm.

Calyx:

*Number of sepals.*—5.

*Color of sepals.*—Closest to RHS 138A.

*Length of sepals.*—0.7-0.8 cm.

*Width of sepals.*—0.2-0.3 cm.

*Sepal shape.*—Lanceolate.

*Apex shape.*—Acute.

*Margins.*—Entire, where not fused.

*Texture, upper surface.*—Glabrous.

*Texture, lower surface.*—Hirsute, pilose.

Reproductive organs:

Gynoecium:

*Pistil.*—1.

*Length.*—2.2-2.4 cm.

*Style color.*—RHS 155C.

*Style length.*—1.6-1.9 cm.

*Stigma color.*—RHS 64C.

*Stigma type.*—Bi-parted; pubescent.

*Ovary color.*—Somewhat lighter than RHS N144A.

*Ovary length.*—0.2 cm.

*Ovary diameter.*—0.15 cm.

Androecium:

*Number of stamens.*—5, with filaments fused to the corolla wall.

*Anther color.*—RHS 155B.

*Length of anthers.*—0.25 cm.

*Level of the anthers in relation to the top of the limb.*—Below.

*Pollen amount.*—None found.

*Fertility/seed set.*—Has not been determined to date.

*Disease/pest resistance.*—Has not been determined to date.

What is claimed is:

1. A new and distinct variety of *Pentas* plant named 'PEZZ0012' substantially as illustrated and described herein.

* * * * *